(12) United States Patent
Hernandez Juanpera

(10) Patent No.: US 12,193,695 B2
(45) Date of Patent: Jan. 14, 2025

(54) LAPAROSCOPIC SURGICAL INSTRUMENT

(71) Applicant: SERVOCAD MICROTRONICS, S.L., Barcelona (ES)

(72) Inventor: Jesus Hernandez Juanpera, Barcelona (ES)

(73) Assignee: SERVOCAD MICROTRONICS, S.L., Barcelona (ES)

( * ) Notice: Subject to any disclaimer, the term of this patent is extended or adjusted under 35 U.S.C. 154(b) by 533 days.

(21) Appl. No.: 17/600,602

(22) PCT Filed: Mar. 17, 2020

(86) PCT No.: PCT/ES2020/070185
§ 371 (c)(1),
(2) Date: Oct. 1, 2021

(87) PCT Pub. No.: WO2020/201596
PCT Pub. Date: Oct. 8, 2020

(65) Prior Publication Data
US 2022/0192691 A1 Jun. 23, 2022

(30) Foreign Application Priority Data
Apr. 2, 2019 (ES) .......................... ES201930528U

(51) Int. Cl.
A61B 17/29 (2006.01)
(52) U.S. Cl.
CPC ...... *A61B 17/29* (2013.01); *A61B 2017/2932* (2013.01)

(58) Field of Classification Search
CPC ............ A61B 17/29; A61B 2017/2932; A61B 18/1445; A61B 2017/2912;
(Continued)

(56) References Cited

U.S. PATENT DOCUMENTS 5,147,373 A * 9/1992 Ferzli ................. A61B 17/0469
606/144
5,261,917 A * 11/1993 Hasson .............. A61B 17/2909
606/208

(Continued)

FOREIGN PATENT DOCUMENTS

EP 1250891 A2 10/2002
EP 2842503 B1 * 11/2016 ............. A61B 17/29

(Continued)

OTHER PUBLICATIONS

International Search Report for patent application PCT/ES2020/070185 issued by the Spanish Patent Office on Jul. 23, 2020, official translation provided.

(Continued)

*Primary Examiner* — Tan-Uyen T Ho
*Assistant Examiner* — Osama Nemer
(74) *Attorney, Agent, or Firm* — Hassan Abbas Shakir; Shakir Law PLLC

(57) ABSTRACT

A laparoscopic surgical instrument is provided with a manual gripping portion provided with three gripping members, one of them being fixed (non-movable) and the other two gripping members being movable and hinged such that each can perform an angular movement, facilitating the use of the tool during surgery.

3 Claims, 6 Drawing Sheets

(58) Field of Classification Search
CPC .... A61B 2017/2929; A61B 2017/2936; A61B 17/2909; A61B 2017/292; A61B 2017/2927; A61B 2017/2939; A61B 2017/294

See application file for complete search history.

(56) References Cited

U.S. PATENT DOCUMENTS

| | | | |
|---|---|---|---|
| 5,275,613 A * | 1/1994 | Haber | A61B 17/29 606/208 |
| 5,281,220 A * | 1/1994 | Blake, III | A61B 17/29 606/174 |
| 5,383,888 A | 1/1995 | Zvenyatsky et al. | |
| 5,752,973 A * | 5/1998 | Kieturakis | A61B 17/29 606/205 |
| 6,159,224 A * | 12/2000 | Yoon | A61B 18/1445 606/147 |
| 6,391,043 B1 * | 5/2002 | Moll | A61B 17/320016 606/174 |
| 6,673,092 B1 * | 1/2004 | Bacher | A61B 17/2909 606/205 |
| 6,730,109 B2 * | 5/2004 | Wollmer | A61B 17/29 606/207 |
| 7,758,608 B2 * | 7/2010 | DiCesare | A61B 17/2909 606/1 |
| 8,764,769 B1 * | 7/2014 | Rodriguez-Navarro | A61B 17/2833 600/114 |
| 9,844,388 B2 * | 12/2017 | Ganter | A61B 17/29 |
| 10,398,459 B2 * | 9/2019 | Ferro | A61B 17/1608 |
| 10,987,120 B2 * | 4/2021 | Heck | A61B 5/6847 |
| 11,737,844 B2 * | 8/2023 | Kingsley | A61B 34/30 606/130 |
| 2002/0072766 A1 | 6/2002 | Hunt et al. | |
| 2002/0177874 A1 | 11/2002 | Nicholas et al. | |
| 2005/0075664 A1 | 4/2005 | Nagase et al. | |
| 2008/0167522 A1 | 7/2008 | Giordano et al. | |
| 2011/0087220 A1 * | 4/2011 | Felder | A61B 18/1445 606/42 |
| 2015/0112382 A1 * | 4/2015 | Hernandez Juanpera | A61B 17/29 606/206 |
| 2020/0305870 A1 * | 10/2020 | Shelton, IV | A61B 17/29 |
| 2020/0323602 A1 * | 10/2020 | Berkelaar | A61B 17/3201 |

FOREIGN PATENT DOCUMENTS

| | | |
|---|---|---|
| ES | 2114962 T3 | 6/1998 |
| ES | 2333509 A1 | 2/2010 |
| ES | 2337984 T3 | 5/2010 |
| ES | 2385518 | 7/2012 |
| WO | 2014044889 | 3/2014 |

OTHER PUBLICATIONS

Written Opinion for patent application PCT/ES2020/070185 issued by the Spanish Patent Office on Jul. 23, 2020, official translation provided.

* cited by examiner

LAPAROSCOPIC SURGICAL INSTRUMENT

OBJECT OF THE INVENTION

The object of the present application is to provide of a laparoscopic surgical instrument.

More specifically, the invention proposes the development of a laparoscopic surgical instrument, which is provided with a manual gripping portion provided with three gripping members, one of them being fixed (non-movable) and the other two gripping members being movable and hinged such that each can perform an angular movement, facilitating the use of the tool during surgery.

BACKGROUND OF THE INVENTION

At present, laparoscopic surgical apparatuses are known for surgery that requires the suturing and ligating of body tissues through incisions made in the walls of the body. However, in a great majority of these apparatuses, the surgical tool acts in a single plane, thus limiting the degrees of freedom and consequently making it difficult for the surgeon to use.

To solve the above problem, a laparoscopic instrument is known which is described in European patent EP-A-1 250 891. This instrument stands out for comprising a pair of joining mechanisms capable of linking, on the one hand, a gripping member to a jaw member and a second gripping member linked to the second jaw member. Additionally, the two gripping members are capable of rotating with respect to a second plane thanks to the structural configuration of the two joining mechanisms.

However, this instrument is relatively complex and the freedom of movement thereof is still limited as it does not allow a 360° rotation of the shaft that joins the jaw members with the gripping members, such that this instrument can be difficult to use during surgery.

To solve all the above problems, an instrument is known which is described in patent publication No. ES 2385518 requested by the same holder. Although this surgical instrument is more comfortable to use compared to prior art devices, in practice it has been observed that in the case of a prolonged time that involves complex movements to be performed during surgery, the user can have difficulty handling it due to the effort that must be made with the movement of the fingers.

It would also be desirable to simplify the assembly of the constructive instrument in order to reduce manufacturing time and costs.

Furthermore, the applicant is not currently aware of an invention that has all the features described in this specification.

DESCRIPTION OF THE INVENTION

The present invention has been developed in order to provide a laparoscopic surgical instrument that is configured as a novelty within the field of application and solves the aforementioned drawbacks, further contributing other additional advantages that will be evident from the description that follows below.

It is therefore an object of the present invention to provide a laparoscopic surgical instrument comprising a manual gripping portion provided with two gripping members being movable and hinged such that each can perform an angular movement, configured to house a user's finger; a work tool (30) provided with two jaws being hinged with each other by a pivoting shaft, that can be handled by means of the gripping portion and; an actuator mechanism capable of transmitting movement from the gripping portion to the work tool, wherein the actuator mechanism comprises two push rods, wherein the distal end of each of the push rods is hingedly coupled to a corresponding jaw and the proximal end is rotatably attached to a corresponding annular body capable of longitudinal movement, such that the push rods are able to rotate, and wherein each gripping member is coupled to a respective annular body by means of connecting rods.

In particular, the invention is characterised in that the gripping portion includes a third fixed gripping member configured to house a user's finger, being coupled to a support part wherein the two push rods are mounted, and located between the two hinged gripping members, the two gripping members being hinged to the third gripping member by means of a shaft.

It is another object of the invention to provide a fully mechanical laparoscopic surgical instrument that can be disposed of after a single use or able to be sterilised for reuse on more than one occasion, which can be very useful for endoscopy and laparoscopy procedures due to the fact that the work tool can adopt multiple positions and/or orientations during the use thereof.

Thanks to these features, it is easier for the user, preferably a surgeon, to handle the tool, improving ergonomics, being constructively simple to manufacture.

Preferably, one of the movable gripping members is defined by a hook-shaped body, such that positioning and/or removal of the finger is facilitated during the use of the instrument.

Additionally, the instrument includes an arched contour extension that extends beyond the area provided for placement of a user's finger.

According to another aspect of the invention, it includes a guiding system to perform the angular movement of each of the jaws, the guiding system being provided with a groove in the shape of a slot present in each of the jaws, in which a protrusion protruding from each of the push rods is slidable. In this way, a greater opening angle is allowed which can be up to 110° and is constructively much simpler than other guiding systems known in the art.

Advantageously, each of the jaws includes stop means that are provided to limit the angular movement thereof.

In a preferred embodiment, the stop means are defined by a terminal area present on the jaw exhibiting two adjacent straight edges (36, 37) forming an obtuse angle with each other, and a straight area present on the facing jaw, provided to abut with one of the straight edges.

The laparoscopic surgical instrument described thus represents an innovative structure with structural and constitutive features hitherto unknown for the purpose for which it is intended, reasons which, together with its practical utility, provide it with a sufficient basis to obtain the privilege of exclusivity that is requested.

Other features and advantages of the laparoscopic surgical instrument object of the present invention will be apparent from the description of a preferred, but not exclusive, embodiment, which is illustrated by way of non-limiting example in the accompanying drawings.

DESCRIPTION OF A PREFERRED EMBODIMENT

Figure 1A:
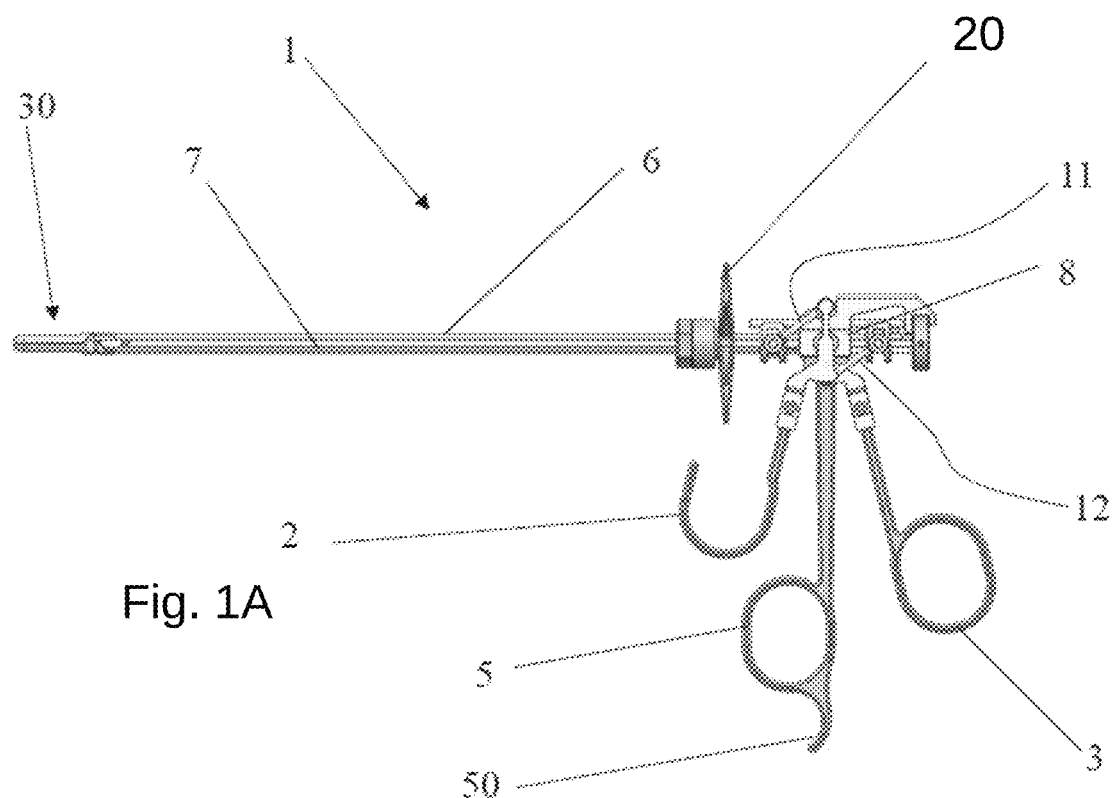
FIG. 1A is a side elevation view of a preferred embodiment of a laparoscopic surgical instrument according to the present invention in a resting position.
Figure 1B:
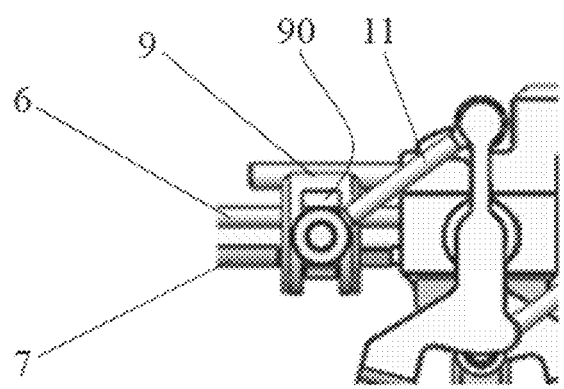
FIG. 1B is an enlarged side view of a portion of FIG. 1A.
Figure 2A:
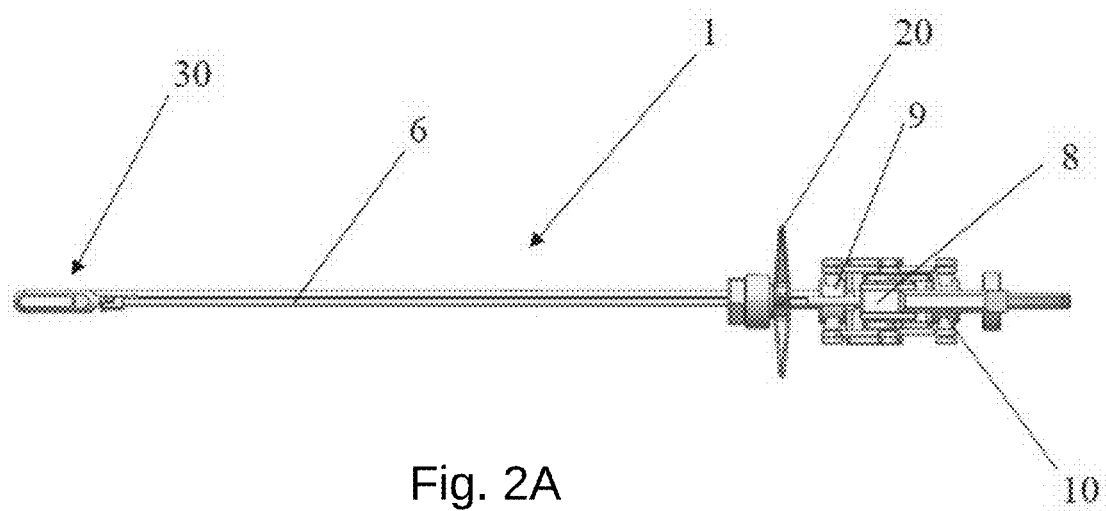
FIG. 2A is a partially cross-sectioned plan view of the surgical instrument shown in FIG. 1A in which some parts have been omitted for clarity reasons.
Figure 2B:
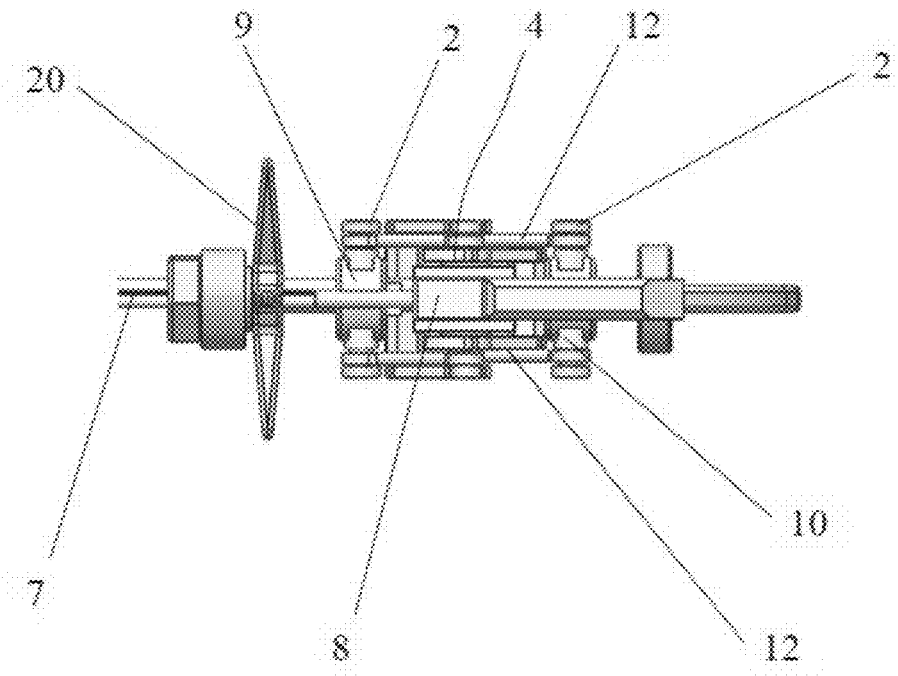
FIG. 2B is an enlarged detailed view of the area where the actuator mechanism is located.
Figure 3:
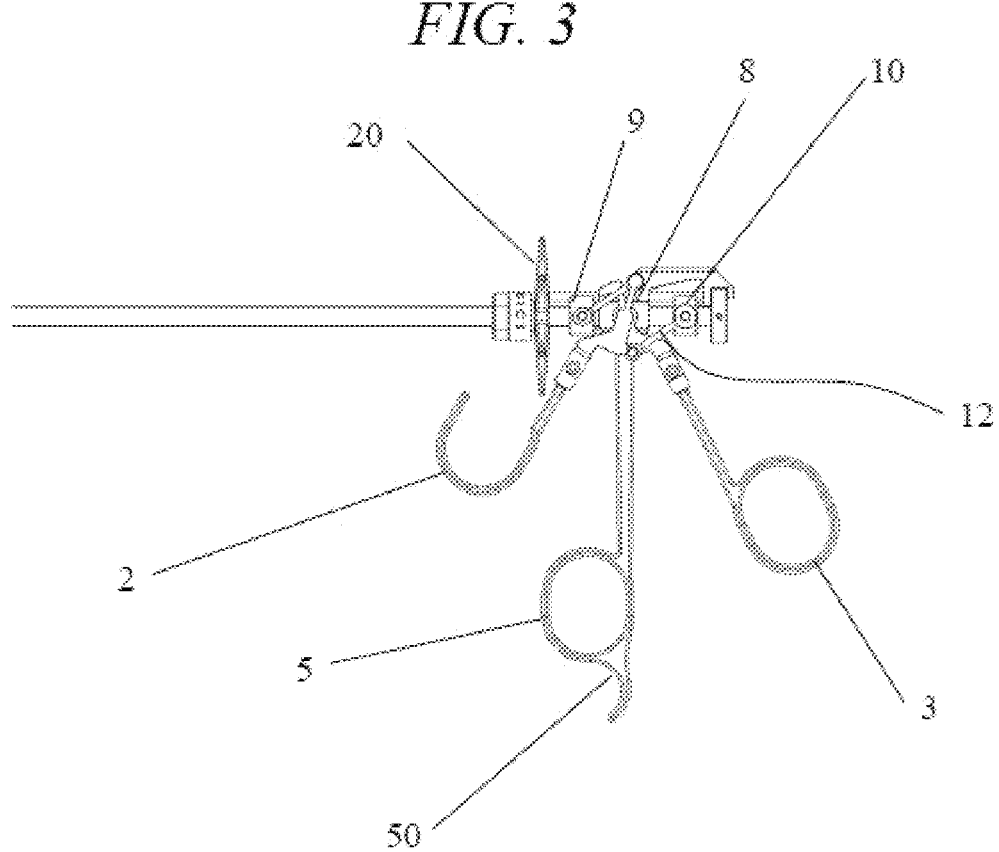
FIG. 3 is a partial side elevation view of the laparoscopic surgical instrument in a second operational position.

In view of the mentioned drawings and according to the numbering used, the figures show a preferred exemplary embodiment of the invention, which comprises the parts and members indicated and described in detail below.

Thus, as can be seen in the attached FIGS. 1A to 4, a laparoscopic surgical instrument, generally indicated with the reference (1), comprises a gripping portion provided with two movable gripping members (2,3) that are hinged to each other by means of a pivoting shaft (4), a work tool (30) provided with two jaws (31, 32) that are hinged to each other by means of a pivoting shaft (35) and an actuator mechanism capable of transmitting the movement from the gripping portion to the work tool (30), said actuator mechanism being described in greater detail below.

Furthermore, the gripping portion includes a third fixed gripping member (5) configured to house a user's finger, being coupled to a support part (8) wherein the two push rods (6, 7) which are detailed below are mounted, and located between the two hinged gripping members, the two gripping members being hinged to the third gripping member by means of a shaft.

One of the movable gripping members (3) and the fixed gripping member (5) exhibit an elongated shape with a rod section that ends with a section by way of a thimble, which have a very similar shape to conventional scissors thimbles, while the remaining movable gripping member (2) is defined by a hook-shaped body, such that the upper portion thereof is open (according to the orientation represented in the figures).

The fixed gripping member (5) includes an extension with an arched contour (50) that extends beyond the area provided for the placement of a user's finger.

Now referring particularly to the actuator mechanism capable of transmitting movement from the gripping portion to the work tool (30), wherein the actuator mechanism comprises two of the aforementioned push rods (6, 7), wherein the distal end of each of the push rods is hingedly coupled to a corresponding jaw and the proximal end is rotatably joined to a corresponding annular body capable of longitudinal movement, such that the push rods (6, 7) are capable of rotating, and wherein each gripping member is coupled to a respective annular body by means of connecting rods (11, 12).

These two annular bodies (9, 10) are movably arranged in a forward and backward axial movement (according to the orientation of FIGS. 1A to 4), wherein each gripping member (2, 3) is coupled to the two annular bodies (9, 10) by means of the set of two connecting rods (11, 12). Each of the connecting rods (11, 12) is coupled through one of the ends thereof to an open portion present in the lateral wall of the annular bodies (9, 10), such that they enable the annular body and consequently the push rod associated with the respective annular body to rotate. The open portion by way of a window through which the end of the connecting rod (11) can slide has been indicated with the numerical reference (90) in FIG. 1B.

A rotating wheel (20) that can be manually actuated enables the push rods (6, 7) to be rotated, the rotating wheel (20) being located in front of the gripping members (2, 3, 5) when the instrument (1) is in a position of use.

The actuator mechanism may be protected by a casing (not shown for clarity purposes) made of any suitable material, such as a plastic material.

Figure 5:
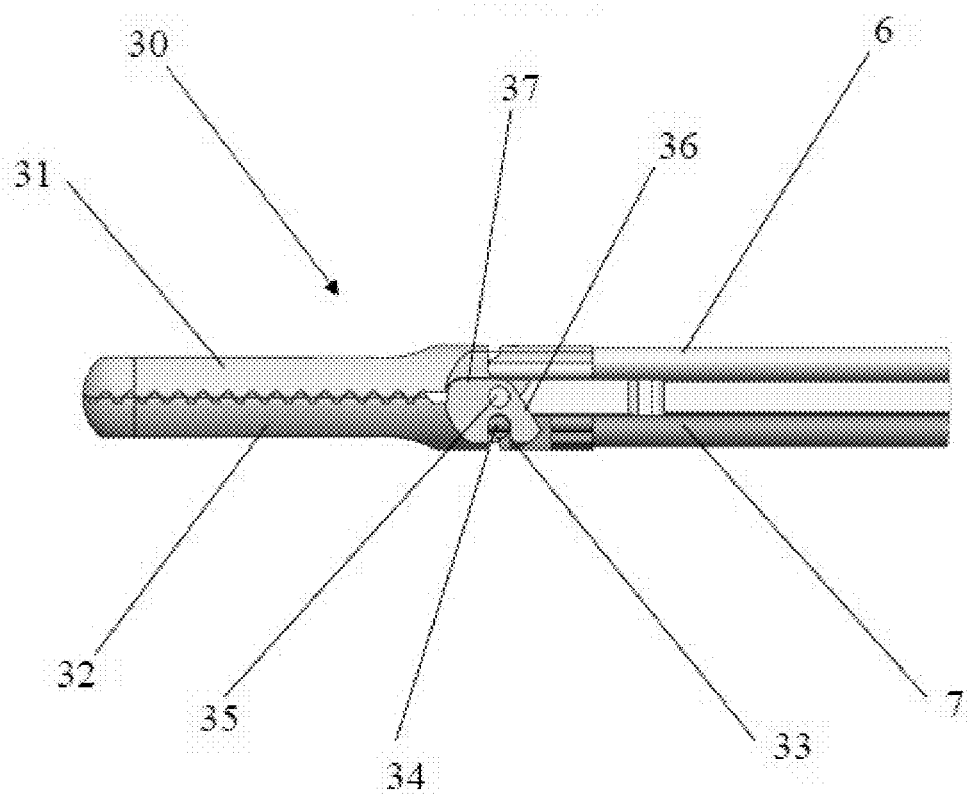
FIG. 5 is a detailed elevation view of the gripping portion of the instrument of the invention with the jaws in a closed position.
Figure 6:
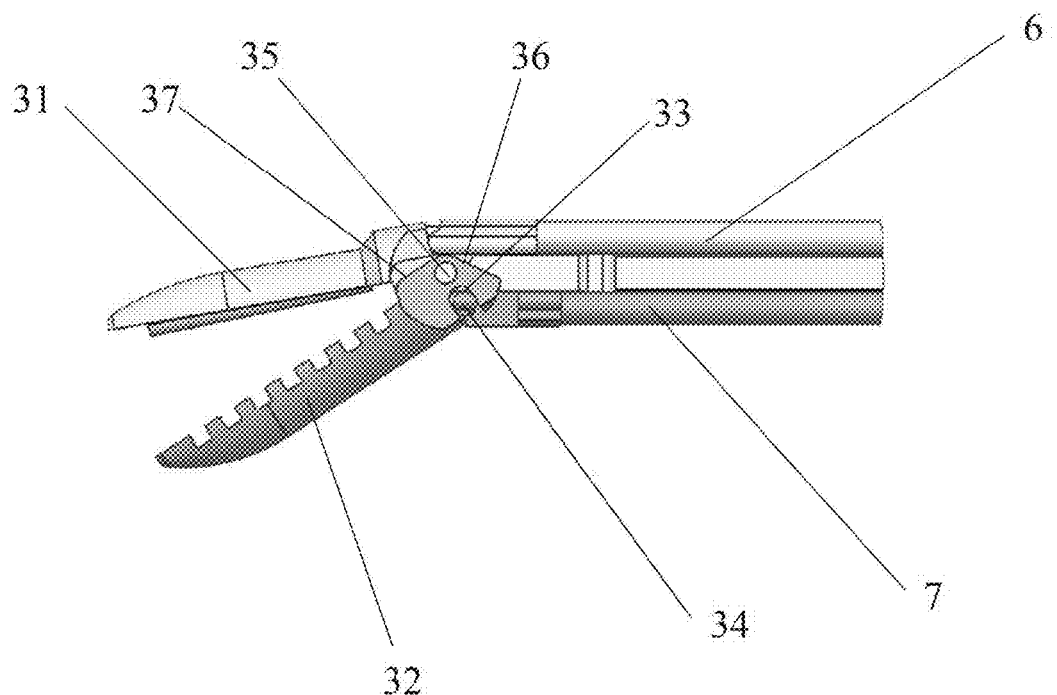
FIG. 6 is a detailed elevation view of the gripping portion with the jaws in an open position.
Figure 7:
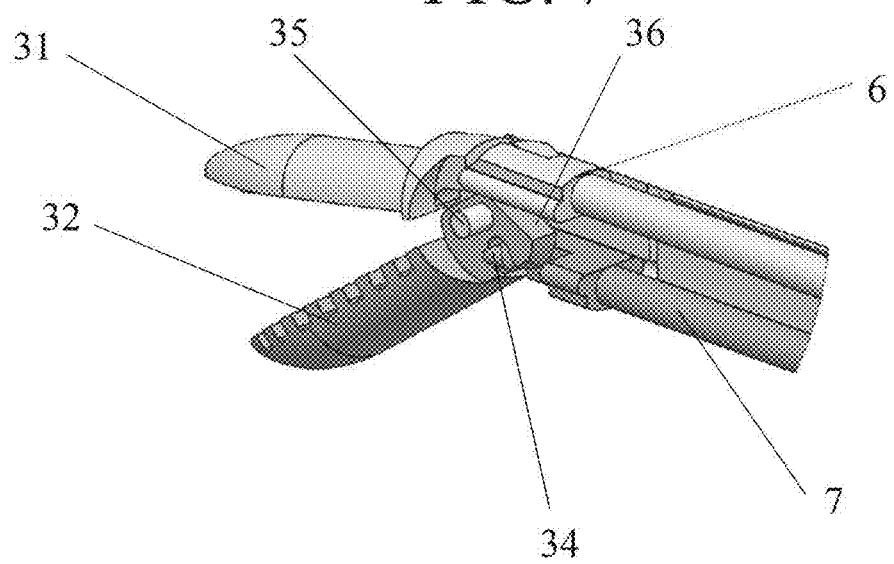
FIG. 7 is a detailed perspective view of the gripping portion of the instrument with the jaws in an open position.

Additionally, a guiding system is provided to perform the angular movement of each of the jaws (31, 32), the guiding system being provided with a groove (33) that is open at one of the ends thereof in the form of a slot present in each of the jaws, in which a projection (34) protruding from the other push rod is slidable, as can be seen more clearly in FIGS. 5 to 7.

Advantageously, each of the jaws (31, 32) includes stop means to limit the angular movement thereof.

These stop means are defined by a terminal area present in the jaw exhibiting two adjacent straight edges (36, 37) forming an obtuse angle with each other, and a straight area present on the facing jaw, intended to abut with one of the straight edges.

It is worth mentioning that the instrument includes a tubular cover located around and along a large portion of the two push rods (6, 7).

At the rear portion of the surgical instrument (1) a connection socket may be arranged, for example of the bipolar type, intended to be connected to a source of electrical current supply, such that electrical voltage can be transmitted if required.

Figure 4:
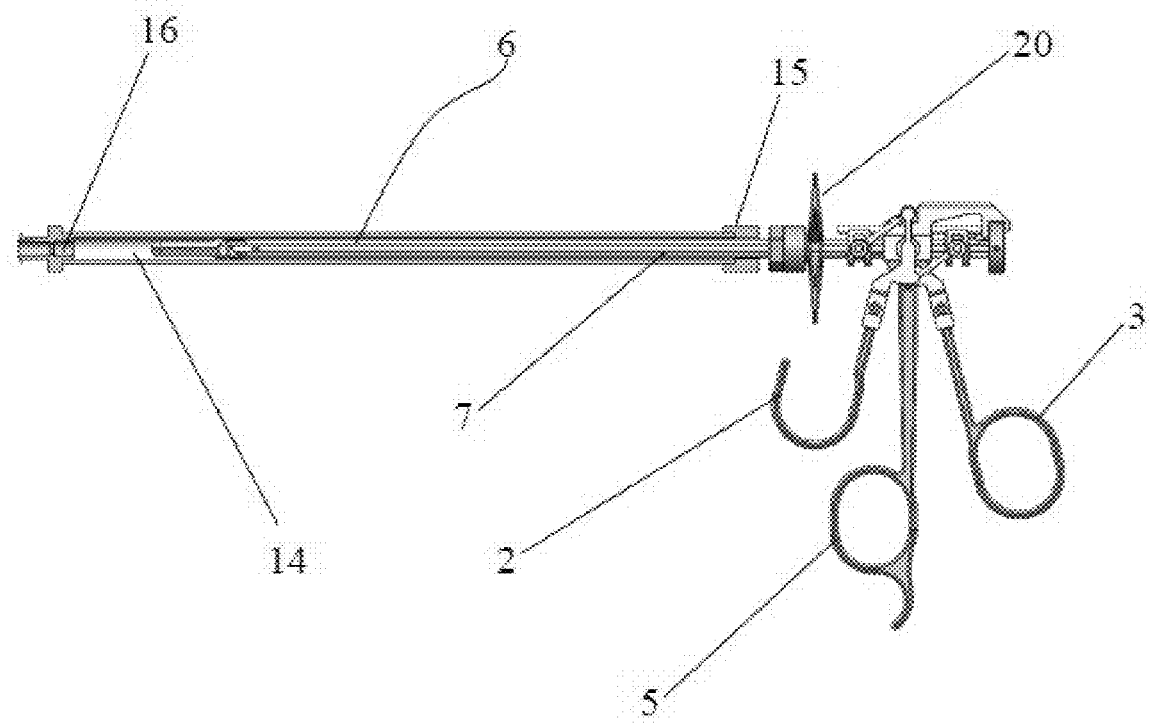
FIG. 4 is a side elevation view of the laparoscopic surgical instrument shown in the previous figures that incorporates a cleaning system.

Finally, as shown in FIG. 4, to clean or sterilise the work tool (30) as well as the two push rods (6, 7), which is usually performed in any type of surgical instrument, a cleaning system can be used comprising an internally hollow tubular member (14) that exhibits an open end with a sealing gasket (15) that adapts to the outer walls of the push rods (6, 7) while the opposite end exhibits an inlet socket (16) provided for coupling to a fluid supply equipment (not shown).

The details, shapes, dimensions and other accessory members used in the manufacture of the instrument of the invention may be conveniently replaced by others that do not depart from the scope of the invention.

What is claimed is:

1. A laparoscopic surgical instrument comprising:
   a manual gripping portion provided with two gripping members being movable and hinged such that each can perform an angular movement, configured to house a user's finger,
   a work tool provided with two jaws being hinged with each other by means of a pivoting shaft, able to be handled by means of the gripping portion,
   an actuator mechanism capable of transmitting movement from the gripping portion to the work tool, wherein the actuator mechanism comprises two push rods, wherein a distal end of each of the push rods is hingedly coupled to a corresponding jaw of the two jaws and a proximal end is rotatably joined to a corresponding annular body capable of longitudinal movement, such that the push rods are capable of rotating, and wherein each gripping member of the two gripping members is coupled to a respective annular body by means of connecting rods, wherein the gripping portion includes a third fixed gripping member configured to house a user's finger, being coupled to a support part wherein the two push rods are mounted, and located between the two hinged gripping members, the two gripping members being hinged to the third gripping member by means of a shaft, each of the connecting rods being coupled through one of ends thereof to an open portion present in a lateral wall of the annular bodies, through which the end of the connecting rod is slidable, such that they enable the annular body and consequently the push rod associated with the respective annular body to rotate, wherein each of the jaws includes stop means to limit the angular movement thereof, and wherein a guiding system is included to perform the angular movement of each of the jaws, the guiding system being provided with a groove in the shape of a slot present in each of the jaws, in which a projection protruding from each of the push rods is slidable.

2. The laparoscopic surgical instrument according to claim 1, wherein one of the movable gripping members is defined by a hook-shaped body.

3. The laparoscopic surgical instrument according to claim 1, wherein the fixed gripping member includes an extension with an arched contour that extends beyond an area provided for the placement of a user's finger.

* * * * *